(12) United States Patent
Larsson et al.

(10) Patent No.: US 7,561,756 B1
(45) Date of Patent: Jul. 14, 2009

(54) PARTICLE SHAPE CHARACTERIZATION FROM 2D IMAGES

(75) Inventors: Mats I. Larsson, Sunnyvale, CA (US); Cetin Kilic, Mountain View, CA (US); Ariana Zimbouski, Berkeley, CA (US); Juan Cai, Fremont, CA (US)

(73) Assignee: Nanostellar, Inc., Redwood City, CA (US)

( * ) Notice: Subject to any disclaimer, the term of this patent is extended or adjusted under 35 U.S.C. 154(b) by 837 days.

(21) Appl. No.: 11/120,462

(22) Filed: May 2, 2005

(51) Int. Cl.
*G06K 9/36* (2006.01)
*G06K 9/00* (2006.01)
*G06T 17/00* (2006.01)

(52) U.S. Cl. .................. 382/285; 382/128; 382/133; 382/254; 345/420

(58) Field of Classification Search .................. 382/285
See application file for complete search history.

(56) References Cited

U.S. PATENT DOCUMENTS

| | | | |
|---|---|---|---|
| 5,671,343 | A | 9/1997 | Kondo et al. |
| 6,049,381 | A | 4/2000 | Reintjes et al. |
| 6,168,775 | B1 | 1/2001 | Zhou et al. |
| 6,522,781 | B1 | 2/2003 | Norikane et al. |
| 6,535,836 | B1 | 3/2003 | Grace |
| 6,552,781 | B1 | 4/2003 | Rompel et al. |
| 6,746,597 | B2 | 6/2004 | Zhou et al. |
| 7,190,832 | B2 * | 3/2007 | Frost et al. .................. 382/173 |
| 7,269,285 | B2 | 9/2007 | Bober et al. |
| 7,352,900 | B2 * | 4/2008 | Yamaguchi et al. ......... 382/192 |
| 7,430,322 | B1 * | 9/2008 | Larsson et al. .............. 382/203 |
| 2007/0127816 | A1 | 6/2007 | Balslev et al. |

OTHER PUBLICATIONS

Wang, Patrick S.P., "High Level Representation and Recognition of 3D Objects from 2D Images", College of Computer Science, Northeastern University, Boston, MA (1997), pp. 1-27.

Liu et al., "Recognition of 3D Objects from 2D Images—Some Issues", SSPR (1996), pp. 240-250.

(Continued)

*Primary Examiner*—Jingge Wu
*Assistant Examiner*—Jose M Torres
(74) *Attorney, Agent, or Firm*—Patterson & Sheridan, LLP

(57) ABSTRACT

Three-dimensional (3D) shapes of particles are characterized from a two-dimensional (2D) image of the particles that is obtained using TEM. The 3D shape characterization method includes the steps of obtaining a 2D image of a batch of nanoparticles, determining 2D shapes of the nanoparticles from the 2D image, and deriving six distributions, each of which corresponds to a 2D shape and a 3D shape associated with the 2D shape. The first size distribution is derived from the nanoparticles having the 2D triangle shape. The second and third size distributions are derived from the nanoparticles having the 2D tetragon shape. The fourth, fifth and sixth size distributions are derived from the nanoparticles having the 2D round shape. Based on these six size distributions, three size distributions, each of which corresponds to one of three 3D shape classes, are estimated. The size distributions corresponding to the 3D shape classes provide a better log-normal distribution than the size distributions corresponding to the 2D shapes.

12 Claims, 8 Drawing Sheets

OTHER PUBLICATIONS

Abou-Chakra et al., "Three-Dimensional Particle Shape Descriptors for Computer Simulation of Non-Spherical Particulate Assemblies", *Advanced Powder Technology*, vol. 15, No. 1 (2004), pp. 63-77.

U.S. Appl. No. 11/016,578, filed Dec. 17, 2004, Cai et al.

Jingyue Liu, "Advanced Electron Microscopy Characterization of Nanostructured Heterogeneous Catalysts," *Microsc. Microanal.*, 2004, vol. 10: pp. 55-76.

L.B. Kiss et al., "New Approach to the Origin of Lognormal Size Distributions of Nanoparticles," *Nanotechnology*, 1999, vol. 10: pp. 25-28.

Temer S. Ahmadi et al., "Shape-Controlled Synthesis of Colloidal Platinum Nanoparticles," *Science*, Jun. 1996, vol. 272: pp. 1924-1926.

Yugang Sun et al., "Shape-Controlled Synthesis of Gold and Silver Nanoparticles," *Science*, Dec. 2002, vol. 298: pp. 2176-2179.

Amanda Crowell, "Shaping Nanoparticles," *Research Horizons: Georgia Institute of Technology*, 1996, vol. 14(2).

C.G. Granqvist et al., "Ultrafine Metal Particles," *Journal of Applied Physics*, May 1976, vol. 47(5): pp. 2200-2219.

* cited by examiner

FIG. 2

| 3D shape \ 2D shape | Tetragon (Tet) Tet from cc | Tetragon (Tet) Tet from tt | Round (R) R from cc | Round (R) R from tt | Round (R) R from to | Triangle (Tri) Tri from tt |
|---|---|---|---|---|---|---|
| Cube Cub-octahedron (cc) | 0.34 | 0 | 0.66 | 0 | 0 | 0 |
| Tetrahedron Truncated Tetrahedron (tt) | 0 | 0.09 | 0 | 0.09 | 0 | 0.82 |
| Truncated Octahedron (to) | 0 | 0 | 0 | 0 | 1.00 | 0 |

FIG. 4

| $N_L$ | $N_U$ | g1(N) | g2(N) | g3(N) | g4(N) | g5(N) | g6(N) |
|---|---|---|---|---|---|---|---|
| 1 | 100 | | | | | | |
| 101 | 200 | | | | | | |
| 201 | 300 | | | | | | |
| 301 | 400 | | | | | | |
| 401 | 500 | | | | | | |
| 501 | 600 | | | | | | |
| 601 | 700 | | | | | | |
| 701 | 800 | | | | | | |
| 801 | 900 | | | | | | |
| 901 | 1000 | | | | | | |
| 1001 | 1100 | | | | | | |
| 1101 | 1200 | | | | | | |
| 1201 | 1300 | | | | | | |
| 1301 | 1400 | | | | | | |
| 1401 | 1500 | | | | | | |
| 1501 | >1501 | | | | | | |

PARTICLE SHAPE CHARACTERIZATION FROM 2D IMAGES

BACKGROUND OF THE INVENTION

1. Field of the Invention

The present invention generally relates to physical characterization of particles and, more particularly, to characterization of three-dimensional (3D) shapes of nanometer-sized particles from two-dimensional (2D) images of the particles.

2. Description of the Related Art

The performance of heterogeneous catalysts is highly dependent on their physical properties, including pore size, surface area and morphology of the carrier, and size and weight of the active catalytic components. As a result, techniques for characterizing the physical properties of heterogeneous catalysts become important when assessing their performance. An article by J. Liu, entitled "Advanced Electron Microscopy Characterization of Nanostructured Heterogeneous Catalysts," Microscopy and Microanalysis, Vol. 10, pp. 55-76 (2004), discusses various advanced electron microscopy techniques used in characterizing model and heterogeneous catalysts, including transmission electron microscopy (TEM), scanning transmission electron microscopy (STEM), and scanning electron microscopy (SEM).

It is understood in the art that the shape of the catalyst surface on which catalysis is carried out plays an important role in determining the performance of the heterogeneous catalyst. U.S. Pat. No. 6,746,597, for example, teaches that the crystal surface [111] of a noble metal catalyst material is selective for hydrogenation and dehydrogenation reactions. However, as the size of the catalyst materials have decreased to nanometer levels, it has become difficult to characterize the shape of the catalyst materials.

There have been some attempts to characterize the shapes of catalyst materials at the nanometer levels. An article by T. Ahmadi et al. entitled, "Shape-Controlled Synthesis of Colloidal Platinum Nanoparticles," Science, Vol. 272, pp. 1924-1926 (June 1996), discloses a method in which 3D shapes of the particles were determined by tilting the samples in the TEM. An article by Y. Sun et al. entitled, "Shape-Controlled Synthesis of Gold and Silver Nanoparticles," Science, Vol. 298, pp. 2176-2179 (December 2002), discloses another method in which 3D shapes of the particles were determined by taking an SEM image of a sample at a tilting angle of 20°.

The methods for characterizing the shape of catalyst materials described above have some limitations. The method employed by T. Ahmadi et al. appears to require tilting and enlargement of each of the nanoparticles being analyzed. Such a process would be too time consuming in practice, especially when a large number of nanoparticles that are less than 5 nm are present. The method employed by Y. Sun et al. addresses tilting of very large nanoparticles (~100 nm) that resemble almost ideal metal cubes. For much smaller size nanoparticles having a number of different non-ideal possible shapes, shape characterization becomes very difficult with existing methods. In fact, the article by J. Liu explains that even for model supported nanoparticles, it is difficult, if not impossible, to obtain statistically meaningful results on the shape distributions of the metal nanoparticles.

SUMMARY OF THE INVENTION

The present invention provides a technique of characterizing 3D shapes of particles from 2D images of the particles. Using the characterized 3D shapes, a more accurate size distribution of nanoparticles can be obtained, especially when TEM images yield a somewhat small sampling set of nanoparticles. Also, the 3D shape information of the nanoparticles can be used in computer models for estimating chemical softness of the nanoparticles.

According to one embodiment, a 2D image of a batch of nanoparticles is obtained using a TEM and the 2D shapes of the nanoparticles are determined from the 2D image. The nanoparticles are classified into one of three 2D shape classes: triangle, tetragon and round, and one of three 3D shape classes. Based on the number of nanoparticles having the 2D triangle shape, the number of nanoparticles that are in the first of the three 3D shape classes is calculated. Based on the number of nanoparticles having the 2D triangle shape and the number of nanoparticles having the 2D tetragon shape, the number of nanoparticles that are in the second of the three 3D shape classes is calculated. Based on the number of nanoparticles having the 2D triangle shape, the number of nanoparticles having the 2D tetragon shape and the number of nanoparticles having the 2D round shape, the number of nanoparticles that are in the third of the three 3D shape classes is calculated.

According to another embodiment, a 2D image of a batch of nanoparticles is obtained using a TEM and the 2D shapes of the nanoparticles are determined from the 2D image. Six size distributions are determined from the nanoparticles. The first size distribution is derived from the nanoparticles having the 2D triangle shape. The second and third size distributions are derived from the nanoparticles having the 2D tetragon shape. The fourth, fifth and sixth size distributions are derived from the nanoparticles having the 2D round shape. Based on these six size distributions, three size distributions, each of which corresponds to one of three 3D shape classes, are estimated. The 3D shape classes include a first 3D shape class including a tetrahedron shape and a truncated tetrahedron shape, a second 3D shape class including a cube shape and a cub-octahedron shape, and a third 3D shape class including a truncated octahedron shape.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 2 shows the association of 2D shapes of a nanoparticle with various 3D shapes;

FIG. 4 is a table used in determining size distributions corresponding to 2D shapes;

DETAILED DESCRIPTION

Figure 1:
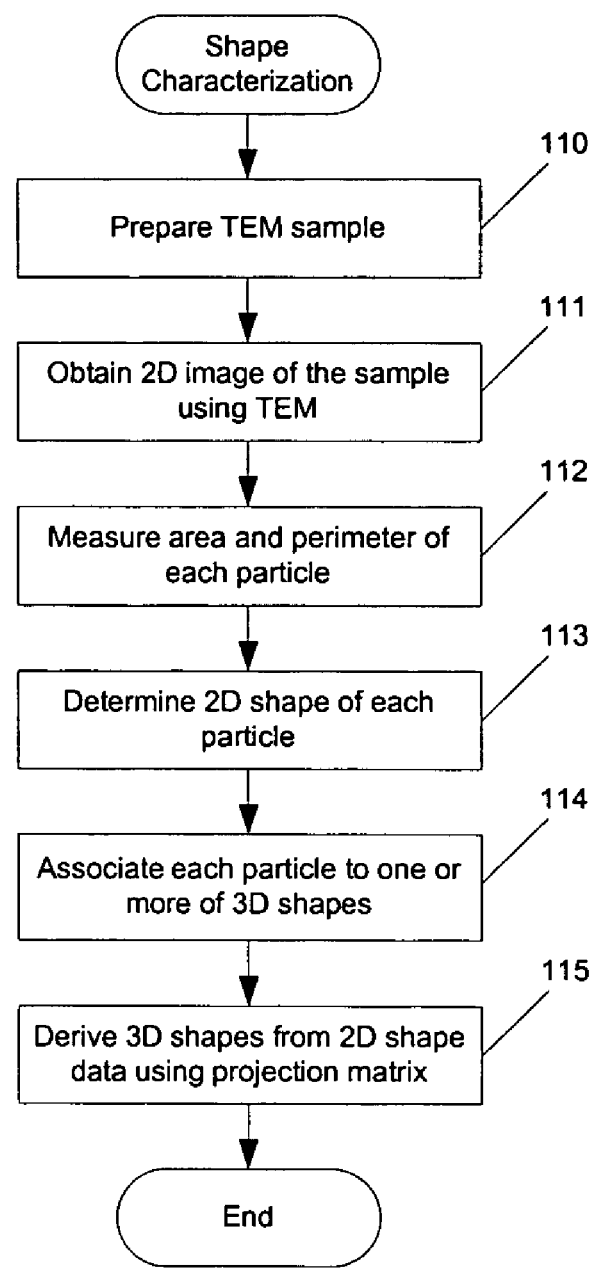
FIG. 1 is a flow diagram illustrating the 3D shape characterization method according to a first embodiment of the invention.

A shape characterization method according to a first embodiment of the invention is illustrated in the flow diagram of FIG. 1. In Step 110, a TEM sample of a batch of nanoparticles is prepared. For this step, the TEM sample preparation method disclosed in U.S. patent application Ser. No. 11/016,578, entitled "Method of Preparing Nanoparticle Samples," filed Dec. 17, 2004, incorporated by reference herein in its entirety, may be used. A TEM image of the sample is then obtained (Step 111). In Step 112, the area and the perimeter of each nanoparticle appearing in the TEM image is measured. Then, in Step 113, the 2D shape of each nanoparticle appearing in the TEM image is determined. The 2D shape is determined to be one of the following major types: tetragon, round, and triangle. The 2D shape determination of a nanoparticle may be performed visually from the TEM image or based on the form factor of the nanoparticle. The form factor of a nanoparticle is derived from the measured area (A) and the measured perimeter (P) of the nanoparticle. The form factor is defined as $4\pi*A/P^2$, which can also be expressed in terms of the harmonic parameter, h, as $2\pi*h/P$, where $h=2A/P$. The form factor by its definition represents the similarity between 2D shapes and circles, which have a form factor of exactly 1. Nanoparticles having form factors less than or equal to 0.75 are classified as triangles. Nanoparticles having form factors greater than or equal to 0.85 are classified as round. Nanoparticles having form factors between 0.75 and 0.85 are classified as tetragons.

In Step 114, each nanoparticle appearing in the TEM image is associated with one or more 3D shapes. The association of a nanoparticle having a particular 2D shape with one or more of the 3D shapes is shown in FIG. 2. The matrix shown in FIG. 2 is referred to as a 3D-to-2D projection matrix. The association is made based on expected 2D projections of nanoparticles having various 3D shapes. When there is more than one possible 2D projection, weight factors are assigned to each of the possible 2D projections, such that the sum of the weight factors for any one 3D shape is one. The weight factors represent the probability of having a particular 2D projection among all possible projections of the 3D shapes. For example, the probability of having a 2D tetragon shape projected from a cube shape and a cub-octahedron shape is 34%, and that of a 2D round shape projected from a cube shape and a cub-octahedron shape is 66%.

The 3D shapes include a 3D tt shape, which is a tetrahedron shape or a truncated tetrahedron shape, a 3D cc shape, which is a cube shape or a cub-octahedron shape, and a 3D to shape, which is a truncated octahedron shape. Each nanoparticle having a 2D triangle shape is associated with a 3D tt shape. Each nanoparticle having a 2D square shape is associated with a 3D cc shape and a 3D tt shape. Each nanoparticle having a 2D round shape is associated with a 3D cc shape, a 3D tt shape and a 3D to shape.

In Step 115, 3D shapes of the nanoparticles in the batch are derived from their 2D shapes based on the relationships between 3D shapes and 2D shapes set forth in the projection matrix. The equations for deriving the 3D shapes based on the 2D shape data are shown below:

$$M_{cc} = \frac{1}{0.34}\left(M^{Tet} - \frac{0.09}{0.82}M^{Tri}\right)$$

$$M_{tt} = \frac{1}{0.82}M^{Tri}$$

$$M_{to} = M^R - \frac{0.66}{0.34}M^{Tet} + \left(\frac{0.32}{0.34} \times \frac{0.09}{0.82}\right)M^{Tri}$$

where $M_{cc}$, $M_{tt}$ and $M_{to}$ represent the number of nanoparticles having 3D cc, tt and to shapes, respectively; and $M^{Tet}$, $M^R$ and $M^{Tri}$ are measured values that represent the number of nanoparticles having the 2D tetragon, round and triangle shapes, respectively. Since $M_{cc}$, $M_{tt}$ and $M_{to}$ cannot be less than zero, the above equations are valid so long as the measured values of $M^{Tet}$, $M^R$ and $M^{Tri}$ meet the following inequalities:

$$M^{Tet} > \frac{0.09}{0.82}M^{Tri}$$

$$M^R > \frac{0.66}{0.34}M^{Tet} - \left(\frac{0.32}{0.34} \times \frac{0.09}{0.82}\right)M^{Tri}$$

Figure 3:
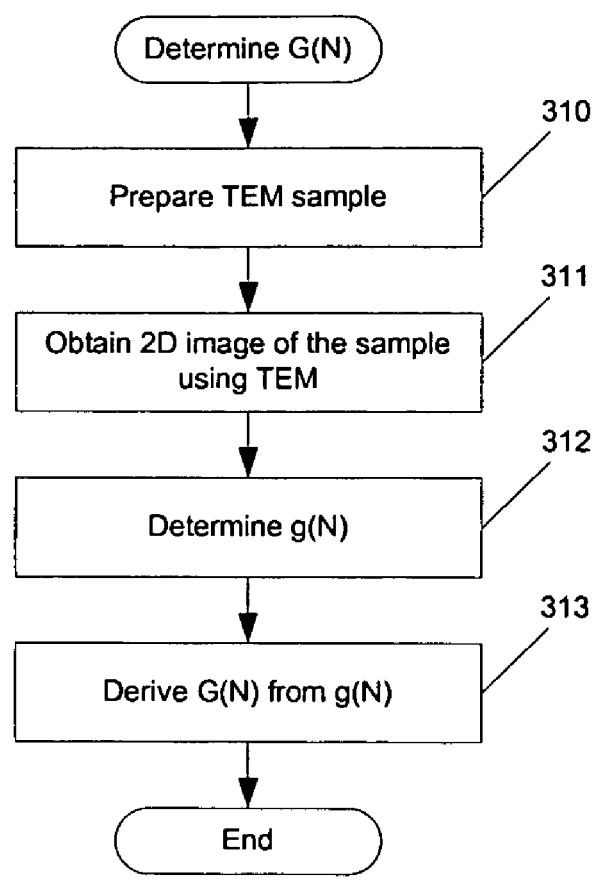
FIG. 3 is a flow diagram illustrating the 3D shape characterization method according to a second embodiment of the invention.

FIG. 3 illustrates a shape characterization method according a second embodiment of the invention. In this method, three distributions, one each for the 3D cc shape ($G_{cc}$), 3D tt shape ($G_{tt}$), and 3D to shape ($G_{to}$), that are defined with respect to the number of atoms (N), are determined from six distributions (g1, g2, g3, g4, g5 and g6), that are defined with respect to the number of atoms (N), based on the following matrix equation:

$$\{G\} = [CP'] \times \{g\}$$

where:

$$\{G\} = \begin{Bmatrix} G_{cc}(N) \\ G_{tt}(N) \\ G_{to}(N) \end{Bmatrix};$$

$$\{g\} = \begin{Bmatrix} g_1(N) \\ g_2(N) \\ g_3(N) \\ g_4(N) \\ g_5(N) \\ g_6(N) \end{Bmatrix};$$

$$[CP'] = \begin{bmatrix} CP(1,1) & 0 & CP(1,3) & 0 & 0 & 0 \\ 0 & CP(2,2) & 0 & CP(2,4) & 0 & 1 \\ 0 & 0 & 0 & 0 & CP(3,5) & 0 \end{bmatrix};$$

$$CP(1,1) = 1 - \frac{0.09}{0.82}\frac{M^{Tri}}{M^{Tet}};$$

$$CP(1,3) = \frac{0.66}{0.34}\left(\frac{M^{Tet}}{M^R} - \frac{0.09}{0.82}\frac{M^{Tri}}{M^R}\right);$$

$$CP(2,2) = \frac{0.09}{0.82}\frac{M^{Tri}}{M^{Tet}};$$

$$CP(2,4) = \frac{0.09}{0.82}\frac{M^{Tri}}{M^R}; \text{ and}$$

$$CP(3,5) = 1 - \frac{0.66}{0.34}\frac{M^{Tet}}{M^R} + \frac{0.09}{0.82}\frac{0.32}{0.34}\frac{M^{Tri}}{M^R}.$$

and where $M^{Tet}$, $M^R$ and $M^{Tri}$ are measured values that represent the total number of nanoparticles having the 2D tetragon, round and triangle shapes, respectively. In order for the matrix equation, $\{G\}=[CP']\times\{g\}$, to hold, the contributions to $\{G\}$ by $\{g\}$ must be greater than zero. It then follows that the measured values of $M^{Tet}$, $M^R$ and $M^{Tri}$ must meet the same inequalities as above:

$$M^{Tet} > \frac{0.09}{0.82}M^{Tri}$$

$$M^R > \frac{0.66}{0.34}M^{Tet} - \left(\frac{0.32}{0.34}\times\frac{0.09}{0.82}\right)M^{Tri}$$

In Step 310, a TEM sample of a batch of nanoparticles is prepared. For this step, the TEM sample preparation method disclosed in U.S. patent application Ser. No. 11/016,578 may be used. A TEM image of the sample is then obtained (Step 311). In Step 312, the six distributions (g1(N), g2(N), g3(N), g4(N), g5(N) and g6(N)) are determined in discrete form. FIG. 4 is a table used in deriving the six distributions in discrete form.

The g1(N) distribution is derived from the nanoparticles having the 2D triangle shape, and based on the knowledge that the 2D triangle shape is associated with a 3D tt shape. The value corresponding to g1($N_L \rightarrow N_U$) represents the number of nanoparticles having the 2D triangle shape that have a number of atoms, as calculated from the 2D area of the nanoparticle and the associated 3D tt shape of the nanoparticle, that fall within the range defined by $N_L$ and $N_U$.

The g2(N) and g3(N) distributions are derived from the nanoparticles having the 2D tetragon shape, and based on the knowledge that the 2D tetragon shape is associated with either a 3D cc shape or a 3D tt shape. The value corresponding to g2($N_L \rightarrow N_U$) represents the number of nanoparticles having the 2D tetragon shape that have a number of atoms, as calculated from the 2D area of the nanoparticle and the associated 3D cc shape of the nanoparticle, that fall within the range defined by $N_L$ and $N_U$. The value corresponding to g3($N_L \rightarrow N_U$) represents the number of nanoparticles having the 2D tetragon shape that have a number of atoms, as calculated from the 2D area of the nanoparticle and the associated 3D tt shape of the nanoparticle, that fall within the range defined by $N_L$ and $N_U$.

The g4(N), g5(N) and g6(N) distributions are derived from the nanoparticles having the 2D round shape, and based on the knowledge that the 2D round shape is associated with a 3D cc shape or a 3D tt shape or a 3D to shape. The value corresponding to g4($N_L \rightarrow N_U$) represents the number of nanoparticles having the 2D tetragon shape that have a number of atoms, as calculated from the 2D area of the nanoparticle and the associated 3D cc shape of the nanoparticle, that fall within the range defined by $N_L$ and $N_U$. The value corresponding to g5($N_L \rightarrow N_U$) represents the number of nanoparticles having the 2D tetragon shape that have a number of atoms, as calculated from the 2D area of the nanoparticle and the associated 3D tt shape of the nanoparticle, that fall within the range defined by $N_L$ and $N_U$. The value corresponding to g6($N_L \rightarrow N_U$) represents the number of nanoparticles having the 2D tetragon shape that have a number of atoms, as calculated from the 2D area of the nanoparticle and the associated 3D to shape of the nanoparticle, that fall within the range defined by $N_L$ and $N_U$.

Figure 5:
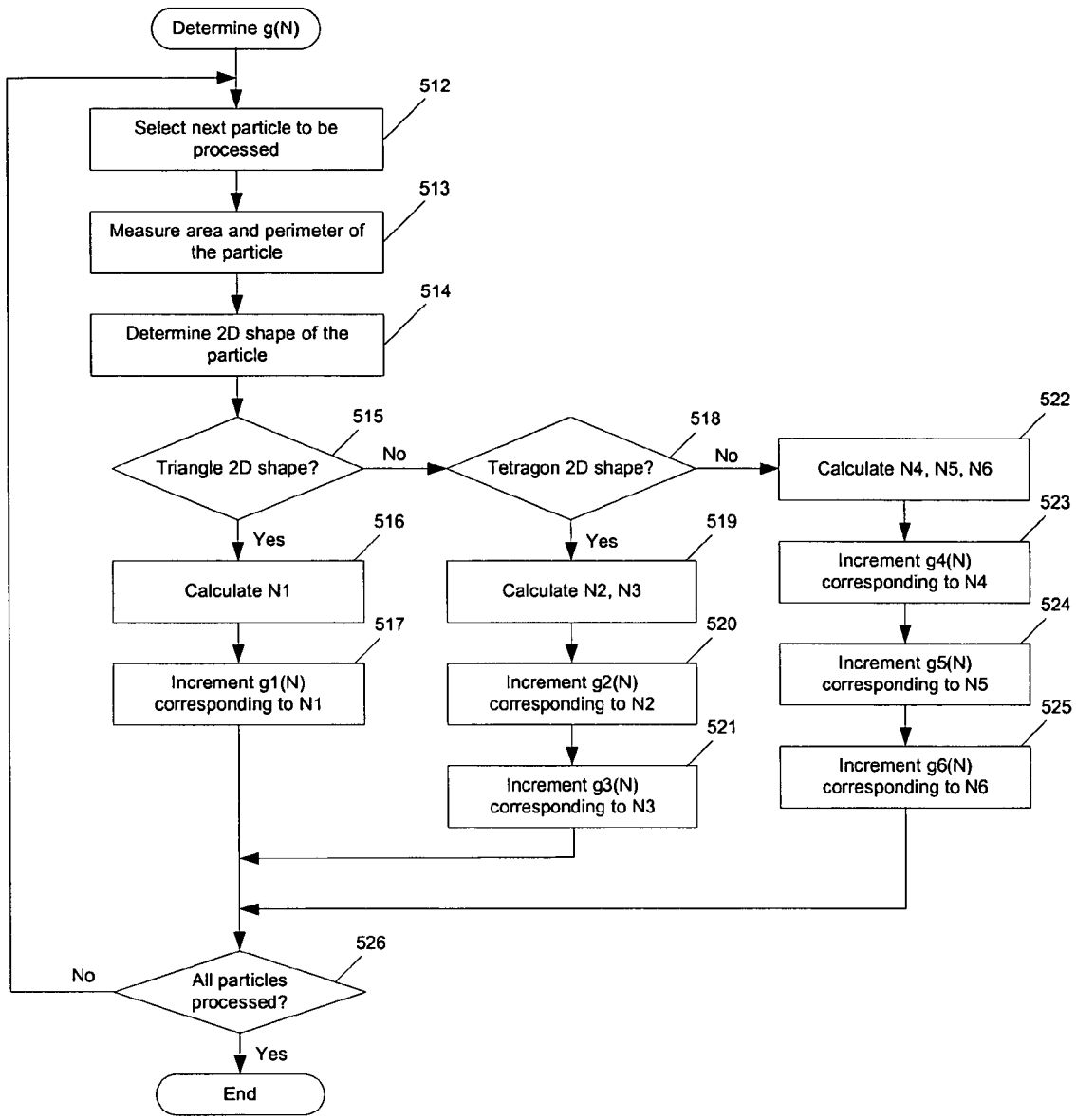
FIG. 5 is a flow diagram illustrating the method of determining the size distributions corresponding to 2D shapes.

FIG. 5 illustrates Step 312 in additional detail. In Steps 512-526, the nanoparticles appearing in the TEM image are processed one at a time. In Step 526, a check is made to see if all nanoparticles have been processed. If all nanoparticles have been processed, the process ends. If not, the process returns to Step 512, where the next nanoparticle to be processed is selected. In Step 513, the area (A) and the perimeter (P) of the nanoparticle selected in Step 512 are measured, and in Step 514, its 2D shape is determined. The 2D shape is determined to be one of the following major types: tetragon, round, and triangle. The 2D shape determination of a nanoparticle may be performed visually from the TEM image or based on the form factor of the nanoparticle, in the same manner as in Step 113 of the first embodiment.

If the 2D shape is determined to be a triangle in Step 515, Steps 516-517 are carried out. According to the projection matrix of FIG. 2, the 2D triangle shape is associated with the 3D tt shape, so in Step 516, the number of atoms in the nanoparticle determined to have the 2D triangle shape in Step 515 is calculated based on this association. The number of atoms, N1, is calculated based on the crystal structure of the element constituting the nanoparticle, its area (A), and the associated 3D shape. For a platinum nanoparticle having the associated 3D tt shape, $N1=0.040*A^{3/2}$. In Step 517, the g1($N_L \rightarrow N_U$) value corresponding to N1 is incremented. Step 526 is then executed to see if all nanoparticles have been processed. If all nanoparticles have been processed, the process ends. If not, the process returns to Step 512, where the next nanoparticle to be processed is selected.

If the 2D shape is determined to be a tetragon in Step 518, Steps 519-521 are carried out. According to the projection matrix of FIG. 2, the 2D tetragon shape is associated with the 3D cc shape or the 3D tt shape, so in Step 519, the number of atoms in the nanoparticle determined to have the 2D tetragon shape in Step 518 is calculated twice, once for the association with the 3D cc shape (N2) and once for the association with the 3D tt shape (N3). The number of atoms is calculated based on the crystal structure of the element constituting the nanoparticle, its area (A), and the associated 3D shape. For a platinum nanoparticle having the associated 3D cc shape, $N2=0.050*A^{312}$. For a platinum nanoparticle having the associated 3D tt shape, $N3=0.023*A^{3/2}$. In Step 520, the g2($N_L \rightarrow N_U$) value corresponding to N2 is incremented, and in Step 521, the g3($N_L \rightarrow N_U$) value corresponding to N3 is incremented. Step 526 is then executed to see if all nanoparticles have been processed. If all nanoparticles have been processed, the process ends. If not, the process returns to Step 512, where the next nanoparticle to be processed is selected.

If the 2D shape is determined to be neither a triangle nor a tetragon, it is determined that the 2D shape is round and Steps 522-525 are carried out. According to the projection matrix of FIG. 2, the 2D round shape is associated with the 3D cc shape or the 3D tt shape or the 3D to shape, so in Step 522, the number of atoms in the nanoparticle determined to have the 2D tetragon shape in Step 518 is calculated three times, once for the association with the 3D cc shape (N4) and once for the association with the 3D tt shape (N5) and once for association with the 3D to shape. The number of atoms is calculated based on the crystal structure of the element constituting the nanoparticle, its area (A), and the associated 3D shape. For a platinum nanoparticle having the associated 3D cc shape, $N4=0.045*A^{3/2}$. For a platinum nanoparticle having the associated 3D ft shape, $N5=0.028*A^{3/2}$. For a platinum nanoparticle having the associated 3D to shape, $N6=0.036*A^{3/2}$. In Step 523, the g4($N_L \rightarrow N_U$) value corresponding to N4 is incremented. In Step 524, the g5($N_L \rightarrow N_U$) value corresponding to N5 is incremented. In Step 525, the g6($N_L \rightarrow N_U$) value corresponding to N6 is incremented. Step 526 is then executed to see if all nanoparticles have been processed. If all nanoparticles have been processed, the process ends. If not, the process returns to Step 512, where the next nanoparticle to be processed is selected.

Figure 6A:
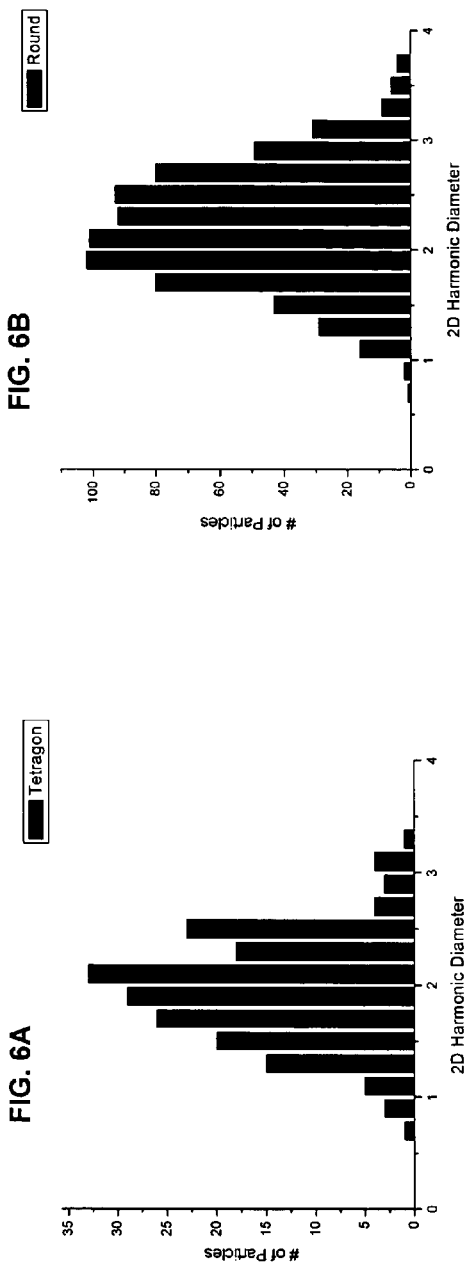
FIGS. 6A-D shows size distributions corresponding to 2D shapes.
Figure 6B:
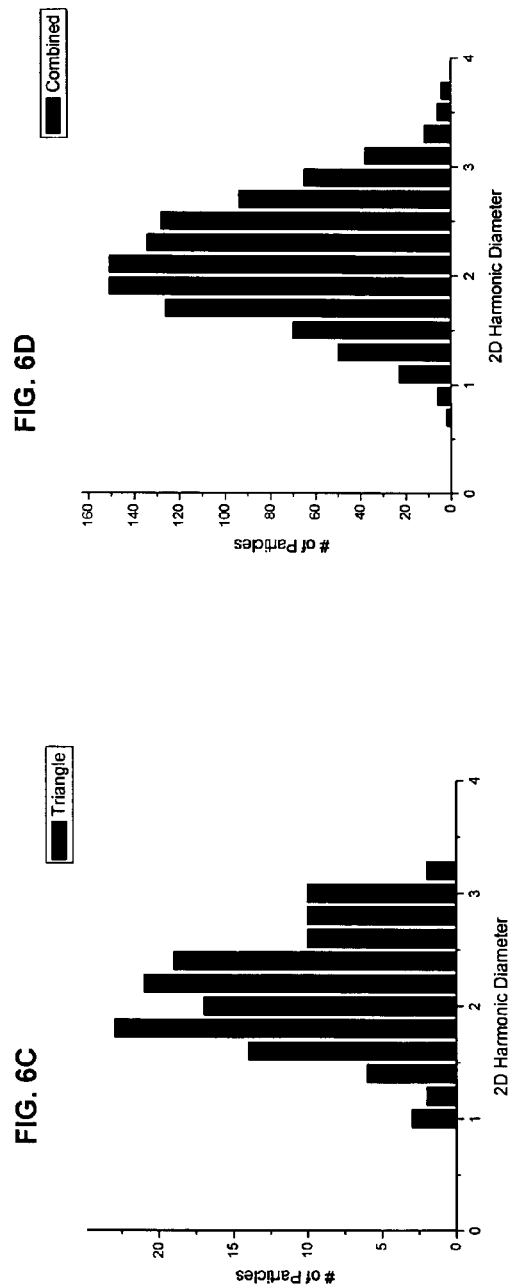
Figure 6C:
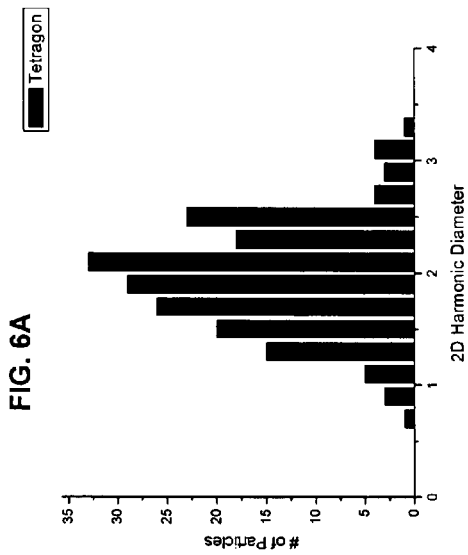
Figure 6D:
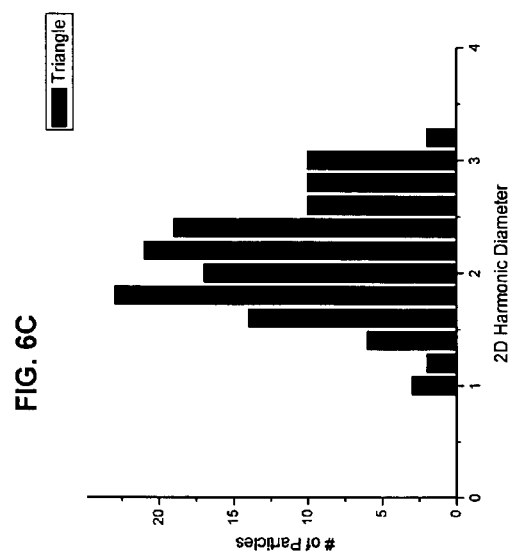
Figure 7B:
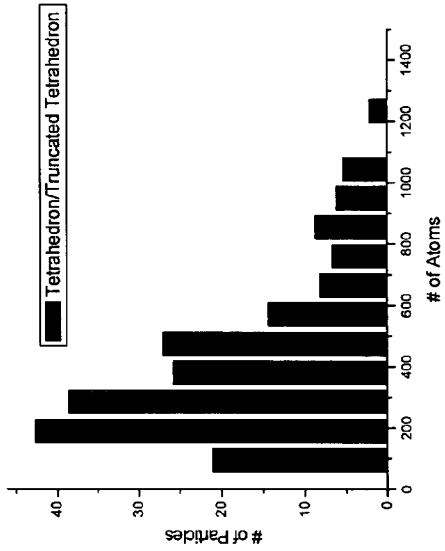
FIGS. 7A-D shows size distributions corresponding to 3D shapes.

After the six distributions, g1(N), g2(N), g3(N), g4(N), g5(N) and g6(N), have been determined in discrete form in accordance with Steps 512-526, the solution to the equation [CP']×{g} is computed for each $N_L \rightarrow N_U$ range to obtain $G_{cc}$, $G_{tt}$ and $G_{to}$, values for each $N_L \rightarrow N_U$ range (Step 313). FIGS. 6A-6C show size distributions corresponding to 2D shapes for a batch of platinum nanoparticles, and FIGS. 7A-7C show size distributions corresponding to 3D shapes that were computed in the above manner. FIG. 6D shows the combined distribution of the size distributions corresponding to 2D shapes, and FIG. 7D shows the combined distribution of the size distributions corresponding to 3D shapes.

Figure 7D:
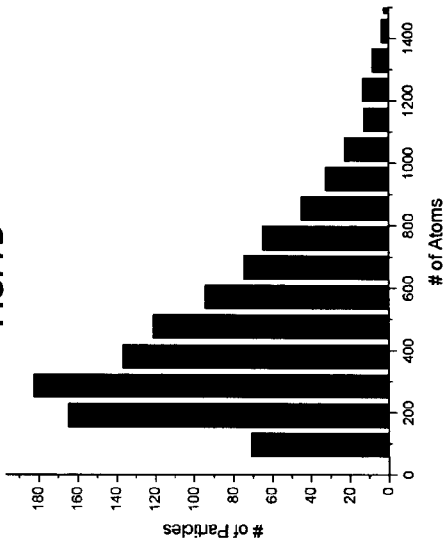
Figure 7A:
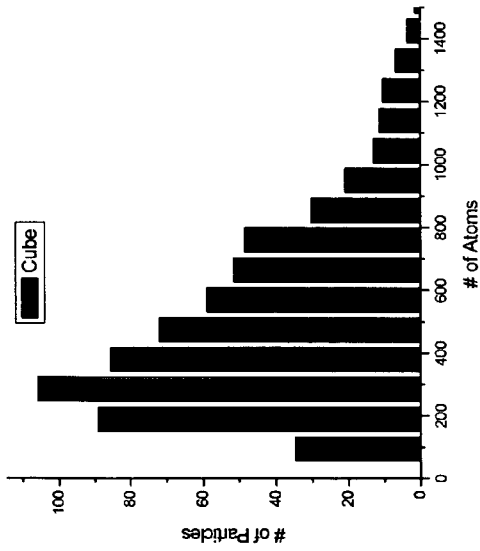
Figure 7C:
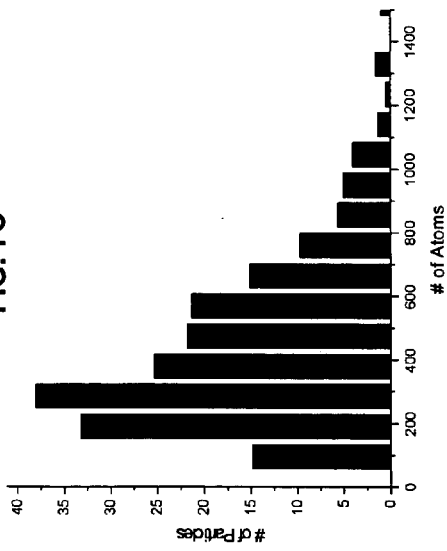
Figure 8:
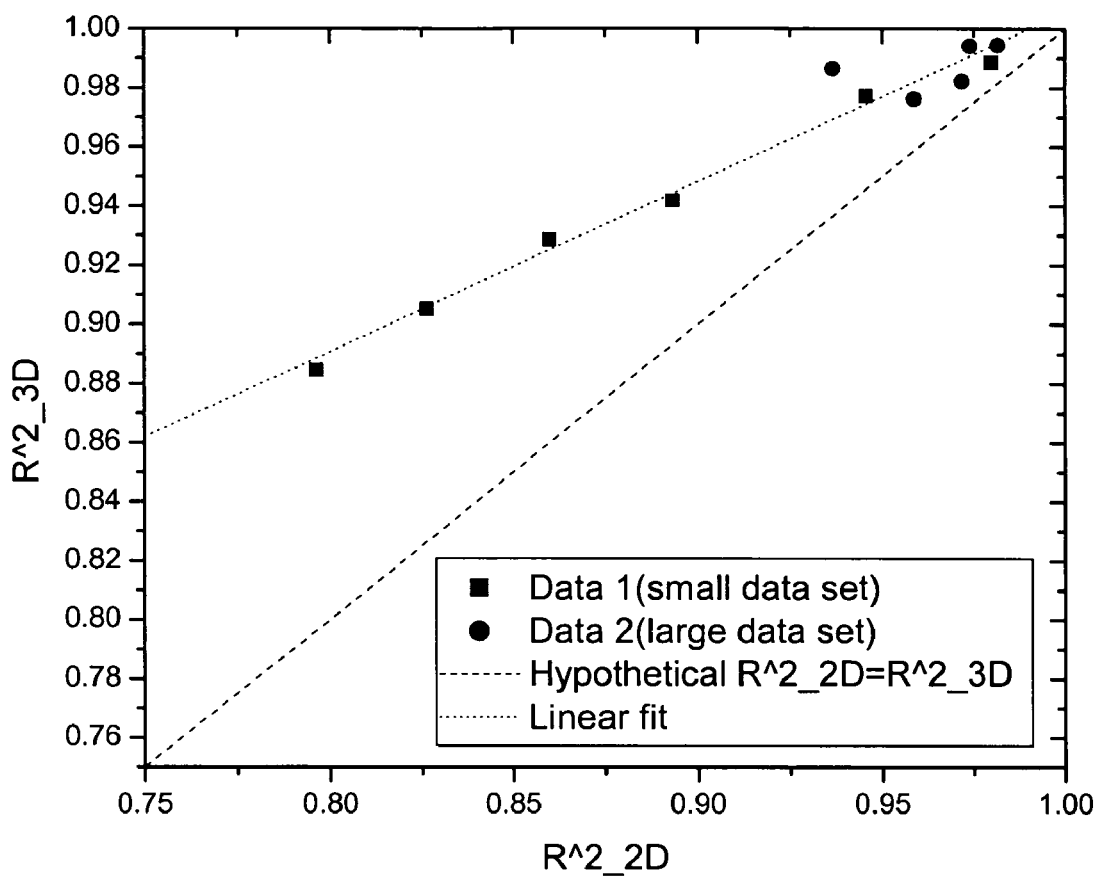
FIG. 8 graphically illustrates the goodness of log-normal fits for size distributions corresponding to 3D shapes and size distributions corresponding to 2D shapes.

The distribution shown in FIG. 7D provides a better log-normal distribution than the distribution shown in FIG. 6D, and this is an indication a more accurate model because, according to published literature, the size distribution of particles is expected to have a log-normal distribution. See, e.g., Kiss, L. B., et al., "New Approach to the Origin of Lognormal Size Distributions of Nanoparticles," Nanotechnology 10 (1999), pp. 25-28; and Granqvist, C. G., et al., "Ultrafine Metal Particles," Journal of Applied Physics, Vol. 47, No. 5 (May 1976), pp. 2200-2219. With the second embodiment of the present invention, the improvement in the log-normal distribution becomes more pronounced for smaller samples. FIG. 8 provides a comparison of the log-normal fit between size distributions determined using 2D shapes and size distributions determined using 3D shapes. It is shown that the improvement in the log-normal fit for small datasets (~100) is greater than for large datasets (~1000). This is noteworthy because nanoscale modeling that relies on log-normal size distributions, e.g., Monte Carlo simulations and atomistic simulations, becomes much easier and more practicable when smaller datasets are used.

While particular embodiments according to the invention have been illustrated and described above, those skilled in the art understand that the invention can take a variety of forms and embodiments within the scope of the appended claims.

What is claimed is:

1. A method of estimating 3D shapes of a batch of particles that has been imaged with an imaging device, said method being performed using a computer and comprising the steps of:
   (a) measuring a 2D size of each of the particles from a 2D image of the particles that has been obtained with the imaging device;
   (b) determining 2D shapes of the particles from the 2D image;
   (c) associating each of the particles to one or more 3D shapes;
   (d) counting the number of particles estimated to have a first of the 2D shapes that are associated with a first of the 3D shapes;
   (e) counting the number of particles estimated to have a second of the 2D shapes that are associated with the first of the 3D shapes;
   (f) counting the number of particles estimated to have the second of the 2D shapes that are associated with a second of the 3D shapes,
   (g) counting the number of particles estimated to have a third of the 2D shapes that are associated with the first of the 3D shapes;
   (h) counting the number of particles estimated to have the third of the 2D shapes that are associated with the second of the 3D shapes;
   (i) counting the number of particles estimated to have the third of the 2D shapes that are associated with a third of the 3D shapes;
   (j) estimating the number of atoms in each particle counted based on its measured 2D size and its associated 3D shape;
   (j) estimating the 3D shapes based on the number of particles counted in step (d), the number of particles counted in step (e), the number of particles counted in step (f), the number of particles counted in step (g), the number of particles counted in step (h), the number of particles counted in step (i), and the estimated numbers of atoms.

2. The method according to claim 1, wherein the first of the 3D shapes is a tetrahedron shape or a truncated tetrahedron shape, and the second of the 3D shapes is a cube shape or cub-octahedron shape, and the third of the 3D shapes is a truncated octahedron shape.

3. The method according to claim 2, wherein the first of the 2D shapes is a triangle shape, and the second of the 2D shapes is a tetragon shape, and the third of the 2D shapes is a round shape.

4. The method according to claim 1, further comprising the step of defining a range for the number of atoms, wherein, in each of the steps (d), (e), (f), (g), (h), and (i) of counting, the particles that have an estimated number of atoms within said range are counted and the particles that have an estimated number of atoms outside said range are not counted.

5. The method according to claim 1, further comprising the step of defining multiple ranges for the number of atoms, wherein each of the steps (d), (e), (f), (g), (h), and (i) of counting includes the step of separately counting the number of particles that have an estimated number of atoms within each of said multiple ranges.

6. A method of estimating a distribution of nanoparticles based on a matrix for mapping 2D shapes onto 3D shapes, comprising the steps of:
   obtaining a 2D image of the nanoparticles with an imaging device; and
   using a computer:
   measuring a 2D size of each of the nanoparticles from the 2D image;
   determining a 2D shape of each of the nanoparticles from the 2D image;
   calculating one or more estimates of the number of atoms in each of the nanoparticles based on the 2D size of the nanoparticle and the 2D shape of the nanoparticle;
   determining a first distribution corresponding to a first 2D shape;
   determining second and third distributions corresponding to a second 2D shape;
   determining fourth, fifth and sixth distributions corresponding to a third 2D shape; and
   estimating a distribution corresponding to a 3D shape based on the matrix and the six distributions of the first, second and third 2D shapes,
   wherein the first distribution is determined based on the estimated numbers of atoms of the nanoparticles having the first 2D shape, and the second and third distributions are determined based on the estimated numbers of atoms of the nanoparticles having the second 2D shape, and the fourth, fifth and sixth distributions are determined based on the estimated numbers of atoms of the nanoparticles having the third 2D shape.

7. The method according to claim 6, wherein the first 2D shape is a triangle shape and the second 2D shape is a tetragon shape and the third 2D shape is a round shape.

8. The method according to claim 7, wherein a first of the 3D shapes is a tetrahedron shape or a truncated tetrahedron shape, and a second of the 3D shapes is a cube shape or cub-octahedron shape, and a third of the 3D shapes is a truncated octahedron shape.

9. The method according to claim 6, wherein each of the six distributions provides a relationship between the number of nanoparticles and the estimated numbers of atoms.

10. The method according to claim 9, wherein the estimated numbers of atoms are divided into M multiple, contiguous and non-overlapping ranges, and for each of the six distributions, the number of nanoparticles corresponding to each of said ranges is counted to produce a 6×M matrix, and wherein the matrix for mapping 2D shapes onto 3D shapes is multiplied with the 6×M matrix to produce a distribution expressed as a 3×M matrix.

11. The method according to claim 6, wherein one estimate of the number of atoms is calculated for each nanoparticle having the first 2D shape, and two estimates of the number of atoms are calculated for each nanoparticle having the second 2D shape, and three estimates of the number of atoms are calculated for each nanoparticle having the third 2D shape.

12. The method according to claim 11, wherein the 2D size measured for each nanoparticle is an area, and each estimate of the number of atoms in a nanoparticle is proportional to the cube of the square root of the 2D area of said nanoparticle.

* * * * *